US012765754B2

(12) United States Patent
Christensen et al.

(10) Patent No.: US 12,765,754 B2
(45) Date of Patent: Oct. 20, 2026

(54) ENDOSCOPE HAVING AN ADJUSTABLE BRAKING MECHANISM

(71) Applicant: AMBU A/S, Ballerup (DK)

(72) Inventors: Martin Johst Christensen, Copenhagen (DK); Jesper Grøndahl Lund, Værløse (DK); Martin Refslund Nielsen, Birkerød (DK)

(73) Assignee: AMBU A/S, Ballerup (DK)

( * ) Notice: Subject to any disclaimer, the term of this patent is extended or adjusted under 35 U.S.C. 154(b) by 779 days.

(21) Appl. No.: 17/986,654

(22) Filed: Nov. 14, 2022

(65) Prior Publication Data

US 2023/0148844 A1 May 18, 2023

(30) Foreign Application Priority Data

Nov. 15, 2021 (DE) ..................... 10 2021 129 717.6

(51) Int. Cl.
*A61B 1/005* (2006.01)
*A61M 25/01* (2006.01)

(52) U.S. Cl.
CPC ....... *A61B 1/0052* (2013.01); *A61M 25/0136* (2013.01)

(58) Field of Classification Search
CPC .. A61B 1/0052; A61B 1/0057; A61B 1/00066
See application file for complete search history.

(56) References Cited

U.S. PATENT DOCUMENTS

2007/0255103 A1* 11/2007 Maruyama ........... A61B 1/0052 600/149
2012/0277535 A1* 11/2012 Hoshino ............ A61B 1/00066 600/146

(Continued)

FOREIGN PATENT DOCUMENTS

EP 2599430 A1 6/2013
EP 2606811 A1 6/2013

(Continued)

OTHER PUBLICATIONS

Search report and English translation for German Patent Application No. 10 2021 129 717.6, dated Aug. 12, 2022.

*Primary Examiner* — Alexandra L Newton
(74) *Attorney, Agent, or Firm* — Faegre Drinker Biddle & Reath LLP

(57) ABSTRACT

An endoscope including steering and braking mechanisms. The braking mechanism includes a manually operable braking control element, a friction element which is axially translatable along a control axis to engage or disengage with the steering mechanism, and a cam pairing transmitting force between the braking control element and the friction element and transforming the braking input into an axial translation of the friction element. The cam pairing has a cam surface and a cam axially contacting the cam surface. The cam surface forms a first ramp section for translating the friction element from a first braking position to an intermediate braking position, a second ramp section for translating it from the intermediate braking position to a second braking position, and an intermediate section forming a tactile structure arranged between the first ramp section and the second ramp section and defining the intermediate braking position.

18 Claims, 7 Drawing Sheets

(56) References Cited

U.S. PATENT DOCUMENTS

| | | | |
|---|---|---|---|
| 2013/0012781 | A1 | 1/2013 | Kaneko |
| 2014/0296640 | A1 | 10/2014 | Hoshino |
| 2014/0343489 | A1 | 11/2014 | Lang et al. |
| 2015/0351610 | A1 | 12/2015 | Fan |
| 2016/0302649 | A1 | 10/2016 | Nakajima |
| 2018/0199796 | A1 | 7/2018 | Lang et al. |
| 2021/0338050 | A1 | 11/2021 | Christensen et al. |
| 2021/0338051 | A1 | 11/2021 | Nielsen et al. |
| 2025/0000344 | A1 * | 1/2025 | Tomberg .............. A61B 1/0051 |

FOREIGN PATENT DOCUMENTS

| | | | |
|---|---|---|---|
| EP | 2837323 | A1 | 2/2015 |
| JP | 4681979 | B2 | 5/2011 |
| WO | 2009/140288 | A2 | 11/2009 |

* cited by examiner

ENDOSCOPE HAVING AN ADJUSTABLE BRAKING MECHANISM

CROSS REFERENCE TO RELATED APPLICATIONS

This application claims priority from and the benefit of German Patent Application No. 10 2021 129 717.6, filed Nov. 15, 2021, which is incorporated by reference herein in its entirety.

TECHNICAL FIELD

The present disclosure relates to a steerable endoscope with a steering brake mechanism, and more particularly, with a steering brake mechanism including a braking control element and a friction element to engage or disengage the steering brake mechanism with the steering mechanism.

BACKGROUND

Steerable endoscopes often have a proximal endoscope handle with an operating wheel for operation by a user and a distal insertion cord including a bending section. The bending section can be bent or manipulated by pulling one or more pulling/steering wires, which extend into the insertion cord of the endoscope and which have distal portions attached to the bending section. In particular, endoscopes are known, which have two steering mechanisms which can be braked individually via two corresponding braking mechanisms, wherein a rotation of a braking knob or lever is transformed via a thread or the like into an axial movement of a friction element to provide a braking force.

The braking mechanisms of such endoscopes usually have two settings: off or on. As such, it is difficult or even impossible to achieve a defined braking force other than full-braking or non-braking. Further, one problem of such endoscopes is a so called "spring back" effect, i.e. the rotation of the steering wheel in a direction opposite to the intended rotation when a user releases the steering wheel. Additionally, such endoscopes often have a complex structure and are therefore expensive in manufacturing and assembly.

For example, US 2015/0351610 A1 discloses an endoscope providing vertical and horizontal bending of a bending portion of an endoscope shaft, said bending being operated via steering wires connected to bending operation knobs. Two corresponding locking mechanisms are provided, wherein a rotation of respective lock operation handles is transformed via a screw into a translational movement along a rotation axis to press a friction pad against the respective bending operation knob. One lock operating handle is provided with an axial protrusion which can selectively engage with recesses in a plate fixed to an endoscope handle. The other lock operation handle is provided with a radial plunger which can selectively engage with recesses in a shaft fixed to the endoscope handle. Several recesses are provided, corresponding to lock, half-lock and free positions.

Further, WO 2009/140288 A2 discloses an endoscope having a handle and a shaft, the latter including a bending portion controllable via steering wires connected to manually controllable knobs. The knobs are connected to drive members which can be locked via frictional brake members actuated via lock levers. The lock levers drive cam members which are inserted into the frictional brake members and have cams protruding radially outwards from a centre ring. The frictional brake members have circumferentially extending elastic brake arms forming braking surfaces at their free outer end portions and cam surfaces contacting the cams at their inner circumference. The cams push the brake arms radially outwards when they glide along the cam surfaces, thus pressing the braking surfaces against the drive members. In the cam surfaces, radially extending detent notches are formed for receiving the cams at defined positions, such as end positions and a partial locking position.

Further prior art can be found in JP 4 681 979 B2, which discloses a handle control part of an endoscope including two hand wheels for driving steering wires, which control bending of a bendable portion of an endoscope insertion portion. Each hand wheel is provided with a friction brake mechanism actuated via a knob or lever. The knob or lever rotates radially extending cam pins, which are guided in an inclined cam groove of a brake member. By rotating the cam pins, the brake member is translated to press a friction disc against the hand wheel. The cam groove has an elastic peripheral portion to allow passage of the cam pins and, at its ends, forms click holes for receiving the cam pins.

EP 2 606 811 A1 and EP 2 837 323 A1 disclose an endoscope having an insertion portion with a portion bendable via steering wires controlled via a manually operable knob. The knob can be locked or braked via a frictional engagement actuated via a brake lever. The brake lever drives a rotatable element forming a circumferentially extending slot defining a cam groove with an inclined surface. Two rotationally fixed plates arranged in the slot are moved towards each other when sliding along the cam groove, clamping a friction plate which is connected to the manually operable knob.

Moreover, from US 2014/0343489 A1 and US 2018/0199796 A1, a control unit of an endoscope handle is known, including two control wheels for the control of steering wires connected to a bending section of an endoscope insertion portion, with the control wheels being provided with brake mechanisms. In one of the brake mechanisms, a brake knob is connected to an axially extending pin via a radially extending peg guided in an inclined groove to transform a rotation of the brake knob into a translation of the pin. The groove may form recesses into which the peg can latch due to a spring force. The pin pushes against a friction member, moving it radially outwards to engage the corresponding control wheel. The other one of the brake mechanism is formed by a frictional sandwich comprising a bushing rotationally fixed to a handle housing, an intermediate brake disc and a lid rotationally fixed to the control wheel. At a periphery of the disc, the bushing and the lid have corresponding indentations and protrusions, which can be brought into and out of engagement, thus allowing a spring to compress the sandwich or to open the sandwich against a reset force of said spring.

BRIEF DESCRIPTION OF THE DISCLOSURE

In view of the above-described problems it is an object of the present disclosure to provide an endoscope, which shall reduce or avoid the disadvantages of the prior art. In particular, it is an object of the disclosure to provide a simple endoscope allowing a setting of defined braking levels.

This object is solved by an endoscope in accordance with claim 1. Advantageous aspects of the present disclosure are claimed in the dependent claims and/or are explained below.

In detail, the present disclosure relates to an endoscope comprising a proximal endoscope handle; an insertion cord extending from the endoscope handle and configured to be inserted into a patient's body cavity, the insertion cord comprising an insertion tube, a bending section and a distal tip unit; a steering mechanism configured to swivel the distal tip unit by bending the bending section, and a braking mechanism configured to brake the steering mechanism, the steering mechanism comprising: a manually operable steering control element, which is provided for receiving a steering input by a user and is rotatable around a control axis, and at least one steering wire, which connects the bending section with the steering control element, and the braking mechanism comprising: a manually operable braking control element provided for receiving a braking input by the user, a friction element which is axially translatable in an axial direction defined by the control axis to engage or disengage with the steering mechanism, and a cam pairing having a cam surface unit forming a cam surface and a cam contacting the cam surface in the axial direction, the cam being connected to or integrally formed with one of the braking control element and the friction element and the cam surface unit being connected to or integrally formed with the other one of the braking control element and the friction element, the cam being configured to slide along the cam surface to transform the braking input into an axial translation of the friction element, wherein the cam surface forms a first ramp section for translating the friction element from a first braking position to an intermediate braking position, a second ramp section for translating the friction element from the intermediate braking position to a second braking position, and an intermediate section forming a tactile structure, being arranged between the first ramp section and the second ramp section and defining the intermediate braking position.

Expressed in other words, an endoscope is provided which has a steering mechanism including a steering control element which is adapted to receive a manual input by a user and is rotatable around a control axis. Said steering mechanism is selectively coupleable/rotationally fixable to an endoscope handle via a braking mechanism. The braking mechanism includes a cam and an inclined cam surface, which contact each other and are moveable relative to each other in a plane orthogonal to the control axis. Due to this relative movement of the cam and the cam surface, the braking mechanism transforms an input operation at a braking control element into a translation of a friction element essentially parallel to the control axis. Thus, the friction element is moved between a first braking position and a second braking position, e.g. pressed against or moved away from a portion of the steering mechanism. The cam surface has a tactile structure defining an intermediate braking position which is neither a full-braking position nor a non-braking position. Thus, in the intermediate braking position, the friction element is translated only partially along the control axis.

The steering control mechanism and the braking control mechanism together may also be abbreviated as "the control mechanism". In general, in the context of this disclosure, for directives such as "circumferentially", "axially" or "radially", the control axis serves as a reference. "Flat" in the context of this application is a surface extending in a plane orthogonal to the control axis, i.e. not having an extension or inclination in the axial direction. An inclination of a surface is, in general, an inclination with respect to a flat surface extending orthogonal to the control axis.

A cam pairing, which provides a contact in the axial direction according to the disclosure, provides a particularly simple structure, which is easy to manufacture and to assemble. In particular, an above described structure of the braking control mechanism and the steering control mechanism makes it possible to assemble most or even all parts concentrically to each other, which is easy to assemble and reduces a need for fine adjustments. Further, providing a tactile structure defining an intermediate braking position makes it easy for the user to set a clearly defined intermediate braking force, which may provide a defined dampening effect and reduce a spring back effect, which has been discussed above. Thus, numerous brake levels can be set by the user, e.g. from no brake to light brake to full brake. A corresponding brake setting will still rely on the rotating movement of the brake lever/the braking control element, however a tactile click (and optionally lock) feature is introduced on the brake lever's/the braking control element's movement from off to on.

Preferably, the cam surface unit is connected to the friction element. Expressed in other words, the cam surface unit may transmit a pressure applied via the cam pairing to the friction element. This is particularly advantageous, since the cam surface unit usually has a large axial thickness in order to accommodate an axial extension of the cam surface. Thus, the cam surface unit is very rigid and can distribute the pressure applied via the cam pairing evenly to the friction element.

Preferably, the braking control element is rotatable around the control axis and the cam surface extends in a circumferential direction around the control axis. The first ramp section and the second ramp section may extend in the circumferential direction and in the axial direction. Expressed in other words, the braking control element may be arranged concentrically with the steering control element and the braking control element may be driven by a rotational input by the user. This provides a structure that is particularly simple to assemble and easy to operate for the user.

It is advantageous if at least two, preferably three, (similar/identical) cam surfaces are provided, which are dimensioned and arranged to form a circle, particularly a full/closed circle around the control axis. E.g. each cam surface may extend circumferentially around an angle of e.g. 180° or 120°. Said differently, the cams and cam surfaces may be evenly distributed around the circumference of the control axis. Thereby, the cam surface unit is stably supported via the cams and a risk of wobbling is minimized, particularly if three cams and cam surfaces are provided.

The manually operable steering element may particularly be a control knob. "Manually operable" means that the steering element is at least partially arranged outside of the endoscope handle such that the user can reach it without disassembly of the endoscope handle. The steering control element may be configured to rotate a shaft connecting the steering control element with a wire drum or sprocket inside the endoscope handle, said wire drum or sprocket being adapted to drive the steering wire. The cam may be non-rotatably connected to or integrally formed with the braking control element. The cam surface unit may be non-rotatably connected to or integrally formed with the friction element. The friction element may be a friction disc or a stack of brake-side friction discs and steering-side friction discs which are alternatingly stacked on each other. The friction element may press against any (particularly axially facing) surface of the steering mechanism, such as a wire drum, the steering control element, a step in a connecting shaft or the like.

The first braking position may be a non-braking position, where the friction element does not provide a frictional lock between the steering control mechanism and the endoscope handle. The second braking position may be a full-braking position, where the frictional element has been moved maximally in the axial direction and is pressed against the steering control mechanism. Alternatively, the first and/or second braking positions may be additional intermediate braking positions.

The tactile structure described above may be any structure which provides a tactile feedback to the user that the intermediate braking position has been reached. For example, the tactile structure may be provided via an abrupt change in inclination or a corner or a flat surface formed between the first ramp section and the second ramp section. Alternatively or additionally, the tactile structure may be provided as an area where a roughness of the cam surface has been increased with respect to the rest of the cam surface.

The cam may be pressed against the cam surface in the axial direction, particularly via a preload applying member such as a spring. Preferably, the preload applying member is separate from the cam surface part. In particular, the preload applying member may press the cam against the cam surface in an area of the intermediate section. This ensures that the cam is pressed against the tactile structure and may not slip over the tactile structure without the user noticing it. Additionally it is thus possible to provide a secure seat of the cam at the intermediate section.

Preferably, the tactile structure may also provide a resistance or stop structure which is configured to hinder or stop the cam and cam surface from being moved by a spring force or the like. For example, the tactile structure may provide an undercut or form locking structure or the tactile structure may include a surface having an angle and/or roughness which acts in a frictional self-locking manner. It is particularly preferable, if the intermediate section forms a projection and/or a recess at least with respect to the first ramp section and optionally with respect to the second ramp section. Expressed in other words, the intermediate structure may form a stopping structure in the circumferential direction, such that, when the cam moves along the cam surface the cam falls behind said stopping structure or is pressed behind said stopping structure.

In particular, the intermediate section may form a first shoulder or step adjacent to the first ramp section, i.e. where the first ramp section and the intermediate section meet. It is preferable if this first shoulder has a relatively large inclination (e.g. compared to an inclination of the first and/or second ramp section) or the step extends axially. In this manner, a secure stop for the cam is provided, particularly since the cam may be pressed towards the first ramp section by the preload applying member. If the inclination of the first shoulder is particularly steep or even parallel to the control axis, a recess or protrusion forming the tactile structure may be shallow/low. In this case, reaching the intermediate section will not result in large variation of braking force due to height differences of the cam surface.

Additionally or alternatively, the intermediate section may form a second shoulder adjacent to the second ramp section. Preferably, the second shoulder has a steeper inclination (extends more in the axial direction) than the second ramp section. Thus, a braking force is increased quickly, when the cam is moved towards the second ramp section. In this manner, a reduction of the braking force caused by the cam slipping e.g. into the recess of the intermediate section is balanced/reversed quickly. In particular, a reference line/virtual extension line extending from and prolonging the first ramp section may essentially be tangential to the second ramp section adjacent to the intermediate section. In this case, a smooth or even linear increase of the braking force may be achieved between a start of the first ramp section and an end of the second ramp section, except for a small decrease at the recess of the intermediate section. In particular, the first ramp section and the second ramp section may have essentially the same inclination. On the other hand, the inclination of the second shoulder is preferably less steep than the inclination of the first shoulder. Moving from the intermediate section towards the second ramp section, the cam has to overcome a greater axial difference than towards the first ramp section. Therefore it is advantageous, if the inclination is relatively flat so that the cam will have an easier climb. By essentially the same inclination it is meant that the inclination can be the same or slightly different, for example at most +/−5, 7, or 10 degrees. Preferably the inclination of the second ramp section is less than the inclination of the first ramp section.

The intermediate section may form an intermediate flat surface, particularly arranged between the first shoulder and the second shoulder. Abrasion particles or the like are unlikely to accumulate at such a flat surface. Thus, via such an intermediate flat surface, it is easy to provide a clearly defined braking force at the intermediate section. Similarly, it is advantageous if the cam surface forms a first flat surface at a position corresponding to the first braking position and/or a second flat surface at a position corresponding to the second braking position. Thus, clearly defined braking forces (including no braking force) can be achieved when the cam contacts the first flat surface or respectively the second flat surface.

The cam may be non-rotatably connected to the braking control element or formed integrally with the braking control element. In particular the latter is inexpensive and simple to manufacture. Preferably, the cam is formed on an inner axial or circumferential surface of the braking control element, further preferably at a radially outer(most) portion of the inner axial surface. In this manner, the cam is very robust and unsusceptible with regard to a load applied thereto via the cam surface.

Preferably, the cam has a contact edge which tapers in a direction towards the cam surface unit. Expressed in other words, at a side facing the cam surface, the contact edge of the cam may be ramp-like at least in one circumferential direction, preferably in both circumferential directions. In particular, the contact edge is a trapezoidal or triangular structure which narrows towards the cam surface. Thus, when operating the braking control element starting from the intermediate braking position, it requires less force to push the cam over the protrusion or out of the recess formed by the intermediate section of the cam surface.

Advantageously, a pressurizing element is provided, which supports a spring element on one axial side and the frictional element on another axial side. Further, the pressurizing element may form a stop surface acting in a direction opposite to the spring element and being adapted to contact a rim portion of the steering control element. Thus, via the pressurizing element several functions can be achieved via a single, simply manufacturable part. In detail, the pressurizing element can pressurize the friction element, and can define a brake release point via the stop surface. In particular, the stop surface may be formed by clip-in arms which are preferably circumferentially (evenly) distributed and may be adapted to snap into engagement structures of the steering control element. In this manner, the pressurizing element may further provide a non-rotatable connection to the steering control element.

It is further preferable, if the braking control element and the cam surface unit engage with each other via a circumferential stopping structure. The circumferential stopping structure preferably includes a circumferentially extending groove providing two opposing circumferential stopper surfaces and an axially extending stopper pin. The circumferentially extending stopper groove and the stopper pin may be slidable with respect to each other in the axial direction and in the circumferential direction. This is a very robust solution for defining a maximum rotation of the braking control element, particularly with respect to the endoscope handle. No other fragile structures have to be used as part of a stopping structure, such as the cam or a stop formed at the cam surface or the like, which may break if the user operates the braking control element too forcefully.

The above described steering mechanism and braking mechanism may also be called a first steering mechanism and a first braking mechanism. Features thereof, such as the steering control element and the like may also be called a first of said feature, e.g. a first steering control element.

Advantageously, the endoscope may further comprise a second steering mechanism configured to swivel the distal tip unit by bending the bending section in a second direction. Optionally, an endoscope comprising the second steering mechanism may be claimed independently. The second steering mechanism may comprise a second manually operable steering control element, which is provided for receiving a second steering input by the user and is rotatable around the control axis, and at least one second steering wire, which connects the bending section with the second steering control element. Further, the second steering mechanism may comprise a second braking mechanism configured to brake the second steering mechanism. The second braking mechanism may comprise a manually operable second braking control element provided for receiving a second braking input by the user and being rotatable around the control axis and a second friction element which is axially translatable in the axial direction to engage or disengage with the second steering mechanism. The second steering mechanism may comprise a second cam pairing having a second cam surface unit forming a ramp and a second cam contacting the ramp in the axial direction. The second cam may be connected to one of the second braking control element and the second friction element and the second cam surface unit may be connected to the other one of the second braking control element and the second friction element. The second cam may be configured to slide along the ramp to transform the second braking input into an axial translation of the second friction element. In particular, the second braking control element and a portion of the endoscope handle form a click interface, said click interface including a click recess or click protrusion as a clicking structure. The clicking structure may be formed at one of the second braking control element and the portion of the endoscope handle. The click interface may further include a spring arm, which is formed at the other one of the second braking control element and the portion of the endoscope handle. The spring arm may be configured to engage with said click recess or click protrusion and to resiliently bend away from said click recess or click protrusion.

Expressed in other words, the endoscope may be provided as a four-way bending endoscope which allows bending of the endoscope in four directions via the (first) steering control element and the second steering control element. Further, the first and second steering control elements can be blocked or braked independently from each other by a dedicated braking mechanism.

Preferably, the second braking control element has a plate-like, in particular annular base portion, which forms the second cam surface or the second cam facing towards one side and which forms the spring arm facing towards an opposing side. Thus, the base portion may have a relatively wide radial width. Further, due to its plate like shape, the base portion may be securely sandwiched between the endoscope handle and the second cam surface unit. Due to this, the base portion may provide good support for the pressure acting on the second cam or cams and preferably no relevant loss of rigidity due to the structure of the spring arms described below occurs.

Advantageously, the spring arm is formed from the base portion of the second braking control element in the manner of a bridge formed between two longitudinal slits. That means the spring arm may be formed integrally with the base portion with both ends being connected to the base portion. The slits may extend completely through the base portion and optionally radially outwards through a rim of the base portion. This is a particularly robust and easily manufacturable structure of the spring arm.

Additionally or alternatively, the problem underlying the present disclosure is solved by a system including the above described endoscope and a monitor connectable to said endoscope.

BRIEF DESCRIPTION OF FIGURES

The following figures illustrate an exemplary embodiment of the disclosure. The disclosure is not limited to the embodiment described below. Other embodiments, combinations of embodiments and modifications may be provided within the scope of protection defined by the claims.

DETAILED DESCRIPTION

Figure 1:
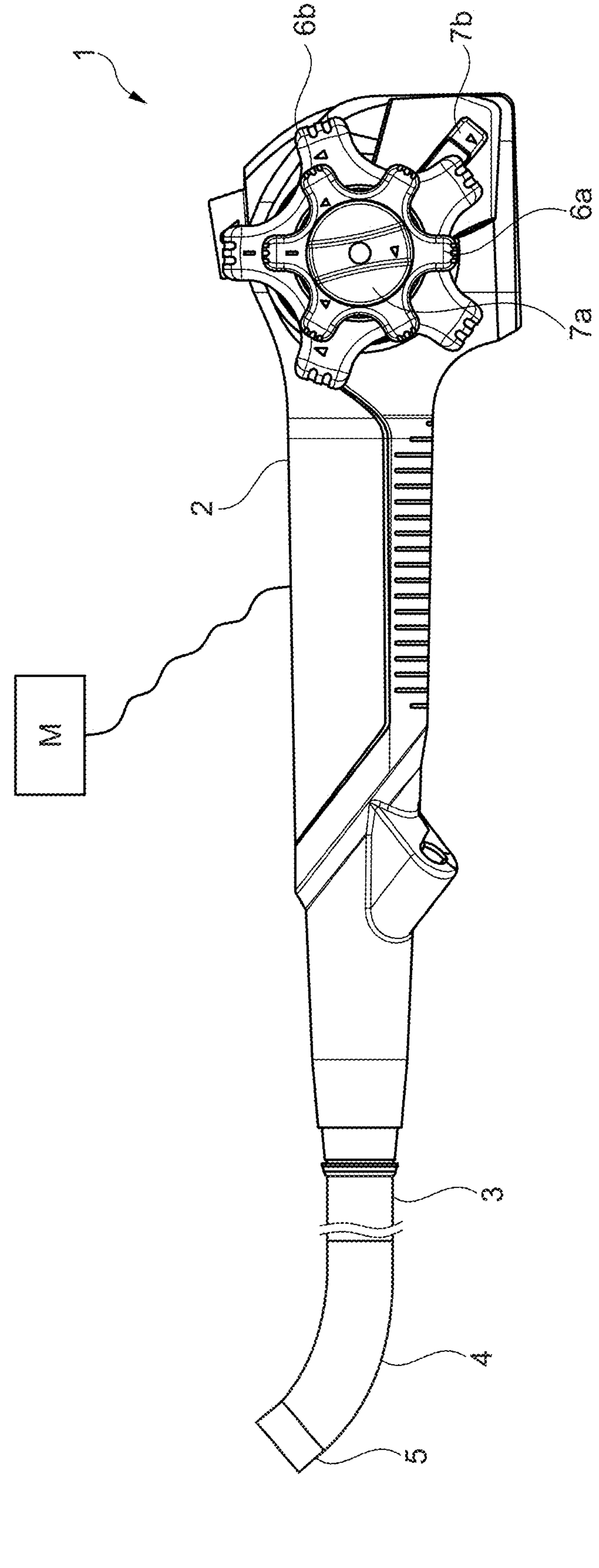
FIG. 1 shows a system including a monitor and an endoscope according to a preferred embodiment of the disclosure.

FIG. 1 shows a schematic view of an endoscope 1, which is preferably a single-use endoscope. The endoscope 1 has a proximal endoscope handle 2 and an insertion cord extending distally from the endoscope handle 2. The insertion cord has an insertion tube 3 connected to the endoscope handle 2. The insertion cord 3 further includes a bending section 4 connected to a distal end of the insertion tube 3 and a distal tip unit 5 connected to a distal end of the bending section 4.

The bending section 4 is configured to perform a bending/pivoting/swiveling movement in four different, preferably orthogonal, directions, i.e. two bending planes. This enables a steering of the endoscope 1. Mounted to the endoscope handle 2, control elements 6*a*, 6*b*, 7*a*, 7*b* for controlling the bending section 4 are provided, which are described in detail below. Further, FIG. 1 shows a monitor M, which is connected or connectable to the endoscope 1, the monitor M and the endoscope 1 forming a system.

The bending/pivoting/swiveling movement in one of the bending planes (in a first and second direction) is controlled by a first steering mechanism including a manually operable first steering control element, or first steering control, 6*a*, in particular formed as a first steering wheel. A first braking mechanism is provided, which has a manually operable first braking control element 7*a*, in particular formed as a knob, and is adapted to brake the first steering mechanism, when said first braking control element, or first braking control, 7*a* is activated by a user.

Further, the bending/pivoting/swiveling movement in the other one of the bending planes (in a third and fourth direction) is controlled by a second steering mechanism including a manually operable second steering control element, or second steering control, 6*b*, in particular formed as a second steering wheel. A second braking mechanism is provided, which has a manually operable second braking control element, or second braking control, 7*b*, in particular formed as a rotatable lever, and is adapted to brake the second steering mechanism, when said second braking control element 7*b* is activated by the user.

Controls, whether steering or braking, can be a wheel, a knob, a lever, a portion of a wheel, and other structures comprising an opening around a central shaft 8 connected to and extending from the handle, rotation of the control around the shaft executing the intended function of steering or braking. Because the controls can be concentric, their position in a stack of elements can limit which external shape the control takes.

Figure 2:
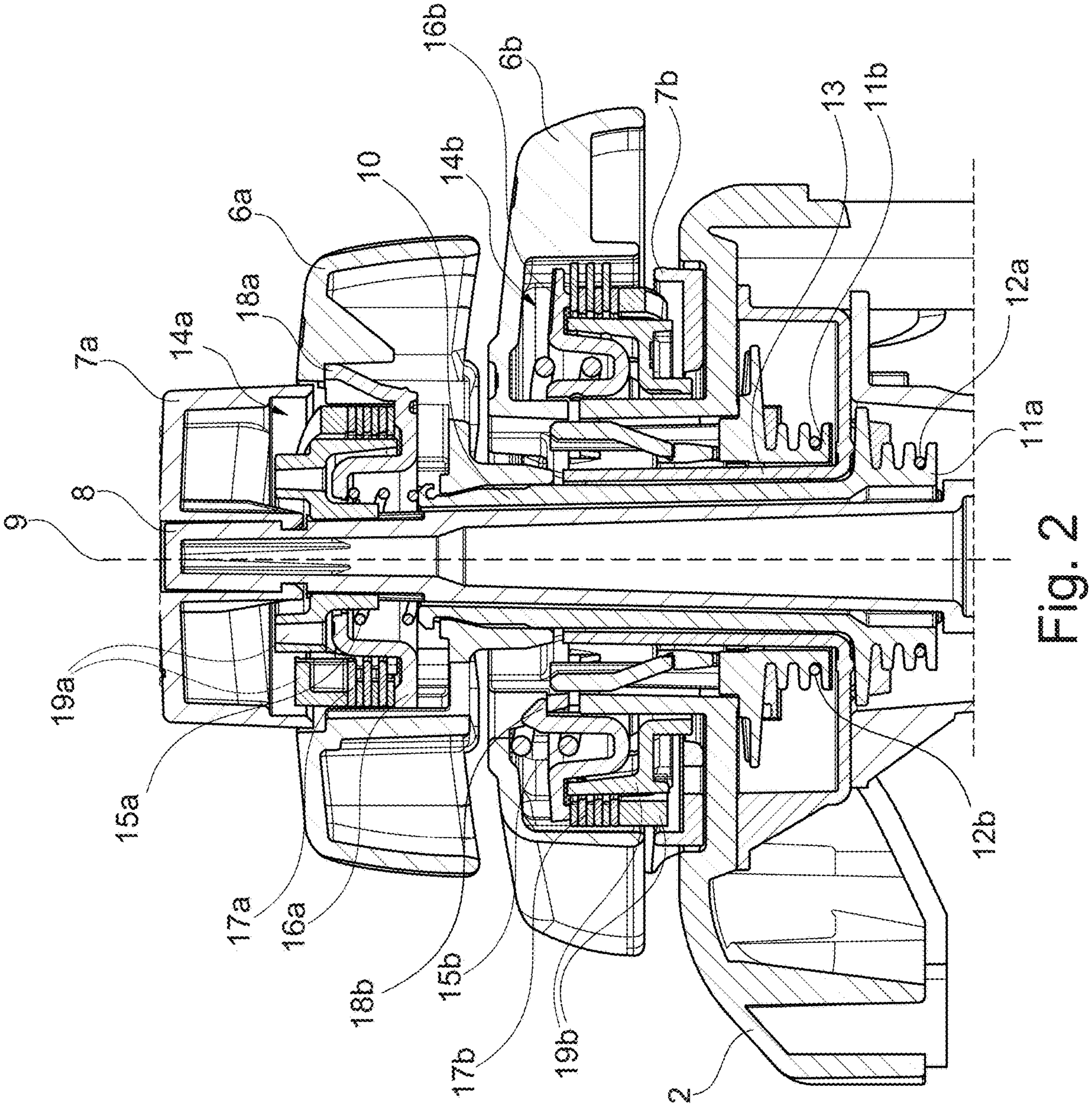
FIG. 2 shows a cross-section of first and second steering and braking mechanisms of the endoscope according to FIG. 1.

The first braking control element 7*a*, the first steering control element 6*a*, the second steering control element 6*b* and the second braking control element 7*b* are rotatably supported by a central shaft 8 shown e.g. in FIG. 2 and are arranged in this order. In this arrangement, the second braking control element 7*b* is adjacent to the endoscope handle 2 (a housing of the endoscope handle 2) and the first braking control element 7*a* is furthest from the (housing of the) endoscope handle 2. The central shaft 8 is fixedly connected to the endoscope handle 2 and defines a control axis 9. In particular, FIG. 2 shows a cross-section of the first braking mechanism and the first steering mechanism (the first control mechanism) as well as the second steering mechanism and the second braking mechanism (the second control mechanism) of the endoscope 1 according to FIG. 1.

The central shaft 8 rotatably supports a hollow shaft 10 of the first steering mechanism, which is integrally formed with a first wire drum 11*a* received within the endoscope handle 2. First steering wires 12*a* are wound around the first wire drum 11 a and extend through the insertion cord to the bending section 4 in order to drive the bending/pivoting/swiveling of the bending section 4 in one of the bending planes. Outside of the endoscope handle 2, the first steering control element 6*a* is non-rotatably connected to the hollow shaft 10. Thus, by rotating the first steering control element 6*a*, the hollow shaft 10 and the first wire drum 11 a are rotated around the control axis 9, pulling or loosening the first steering wires 12*a* to control the bending section 4.

Surrounding the hollow shaft 10, an intermediate support portion 13 is provided, which is fixedly connected to the endoscope handle 2 and rotatably supports the second steering control element 6*b*, which is arranged outside the endoscope handle 2 and is non-rotatably connected to a second wire drum 11*b* arranged inside the endoscope handle 2. Second steering wires 12*b* are wound around the second wire drum 11*b* and extend through the insertion cord to the bending section 4 in order to drive the bending/pivoting/swiveling of the bending section 4 in the other one of the bending planes. The second wire drum 11*b* is fixedly connected to the second steering control element 6*b*. Thus, by rotating the second steering control element 6*b*, the second wire drum 11 b is rotated around the control axis 9, pulling or loosening the second steering wires 12*b* to control the bending section 4.

The following description refers to "the braking mechanism" and details first features of the first braking mechanism and second features of the second braking mechanism which are similar to each other. Such similar features are denoted both with reference signs including the letter "a" corresponding to the first braking mechanism and with reference signs including the letter "b" corresponding to the second braking mechanism.

The (selectively first or second) braking mechanism is described in detail below with reference to FIGS. 2 to 6. In particular, as can be seen in FIG. 2, the braking mechanism includes the (selectively first or second) braking control element 7*a*, 7*b*, a (selectively first or second) friction fit assembly 14*a*, 14*b* and a (selectively first or second) spring 15*a*, 15*b*. The friction fit assembly 14*a*, 14*b* and the spring 15*a*, 15*b* are accommodated in the (selectively first or second) steering control element 6*a*, 6*b*. The spring 15*a*, 15*b* is axially supported on the steering control element 6*a*, 6*b* and preloads the friction fit assembly 14*a*, 14*b* towards the braking control element 7*a*, 7*b*.

The friction fit assembly 14*a*, 14*b* includes a (selectively first or second) pressurizing element 16*a*, 16*b*, which on one axial side forms a trough for accommodating the spring 15*a*, 15*b* and supporting it in the axial direction. Axially opposite and in particular radially outwards with respect to its trough, the pressurizing element 16*a*, 16*b* forms a flat supporting surface, where a (selectively first or second) stack of friction discs 17*a*, 17*b* is supported. This stack of friction discs 17*a*, 17*b* is a friction element according to the disclosure and is described in detail below.

Further, the pressurizing element 16*a*, 16*b* forms a stop and engagement structure in the form of (selectively first or second) clip-in arms 18*a*, 18*b* which are adapted to resiliently snap into an engagement structure formed by the steering control element 6*a*, 6*b*. The clip-in arms 18*a*, 18*b* are adapted to contact a rim of the steering control element 6*a*, 6*b* in an axial direction to prevent the spring 15*a*, 15*b* from pushing the pressurizing element 16*a*, 16*b* out of the steering control element 6*a*, 6*b*. Further, the clip-in arms 18*a*, 18*b* engage with the pockets or openings formed in the steering control element 6*a*, 6*b* in such a manner, that a relative rotation thereof is prevented and an axial displacement thereof is possible.

Figure 3:
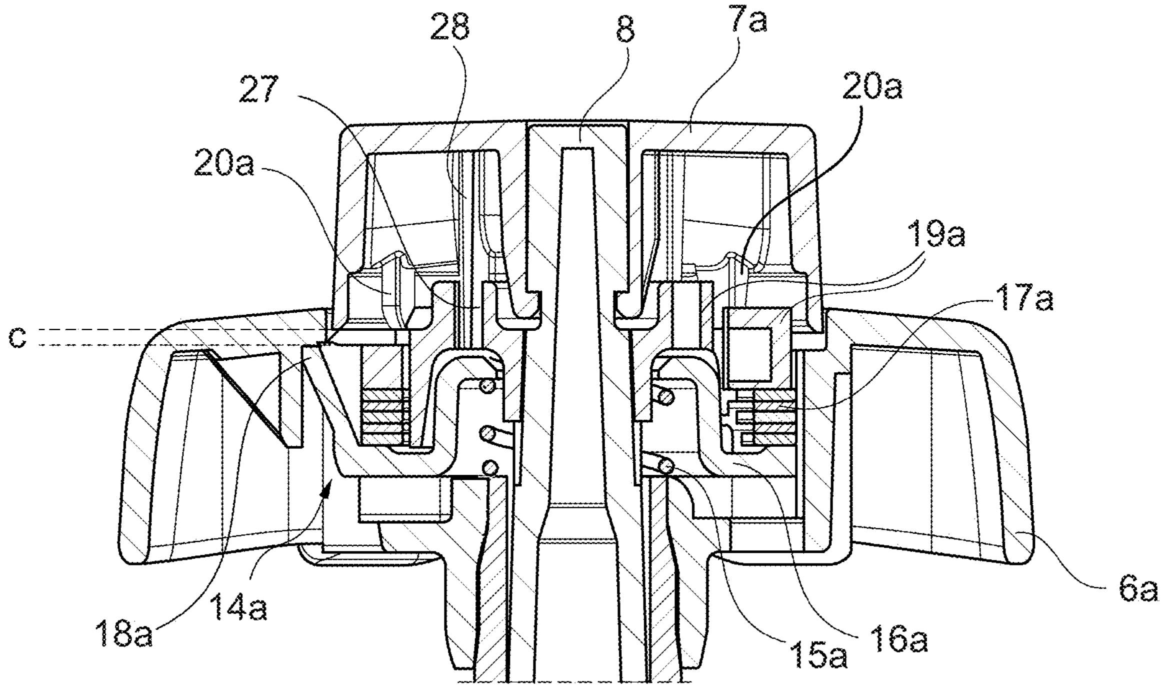
FIG. 3 shows a sectional view of the first braking mechanism according to FIGS. 1 and 2 in a non-braking state and FIG. 4 shows a braking state thereof.
Figure 4:
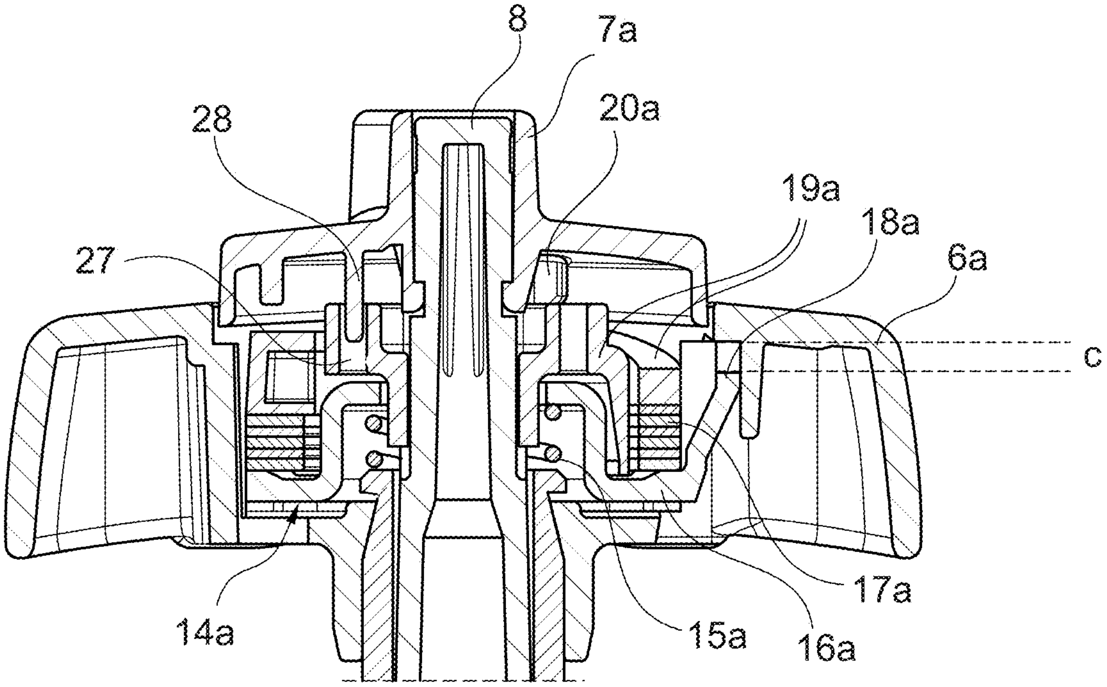
Figure 5:
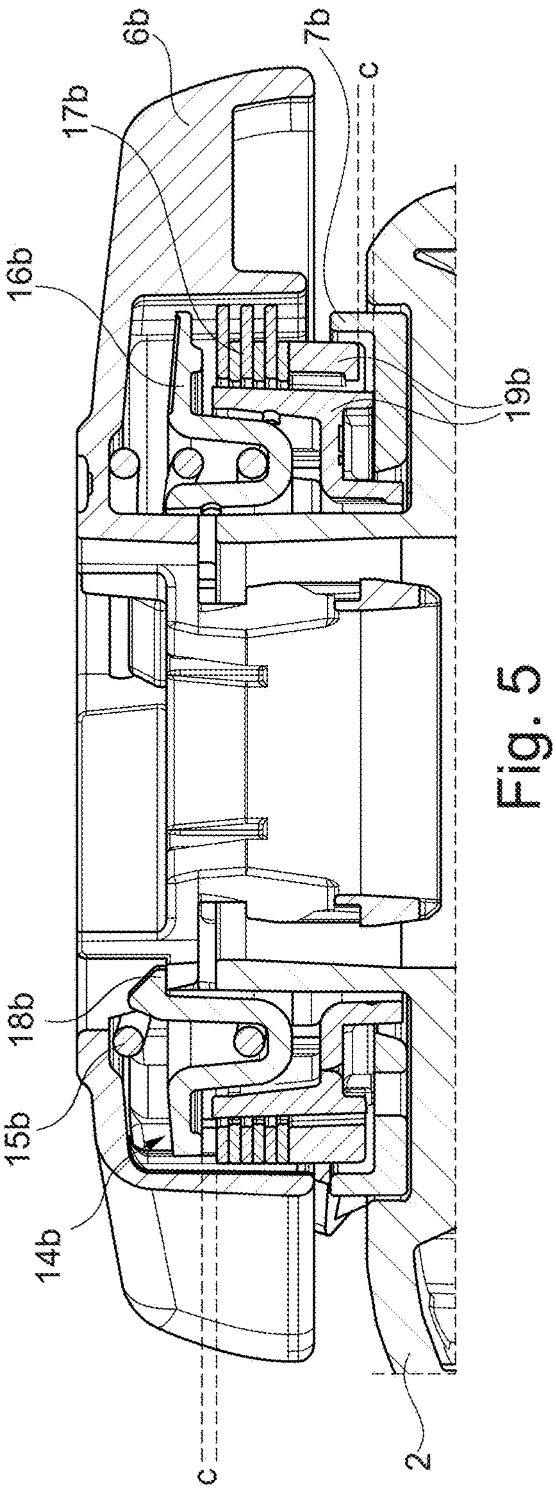
FIG. 5 shows a sectional view of the second braking mechanism according to FIGS. 1 and 2 in a non-braking state and FIG. 6 shows a braking state thereof.
Figure 6:
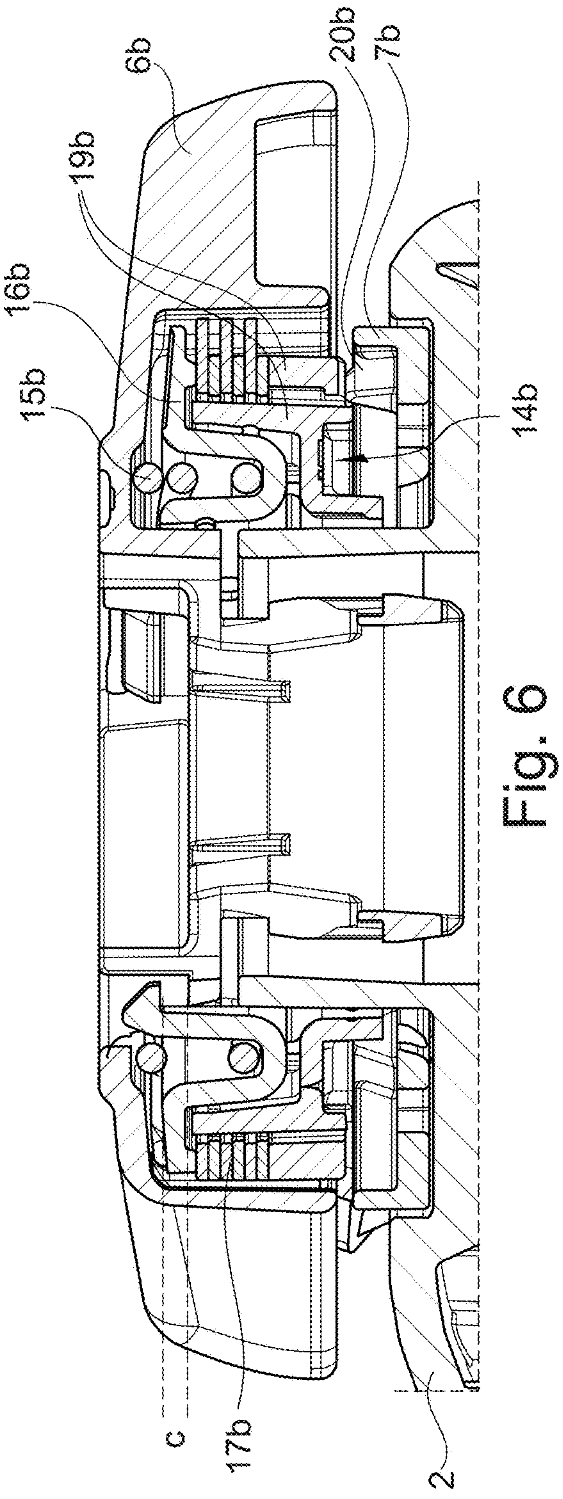
Figure 7:
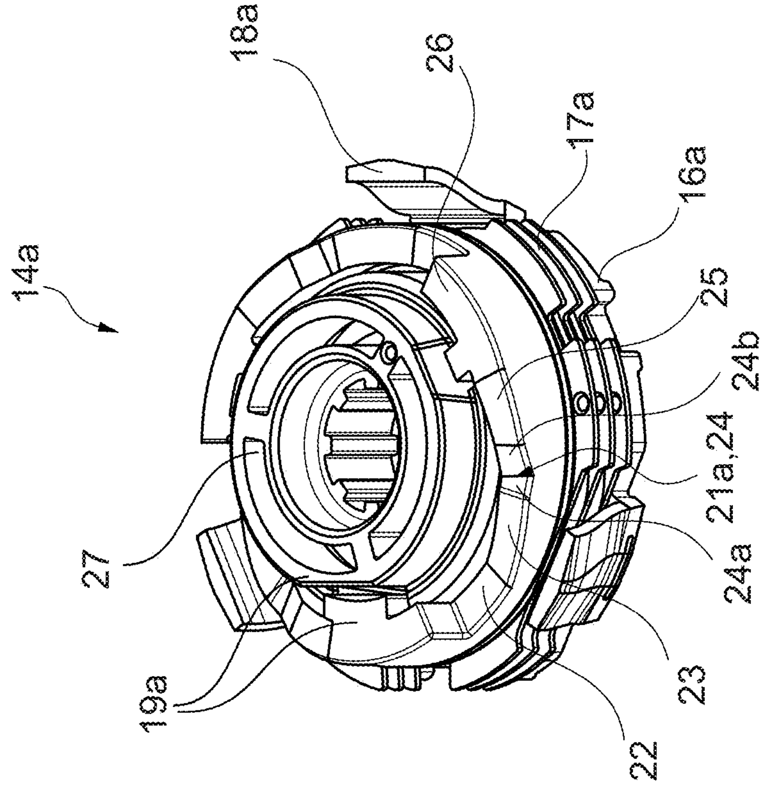
FIG. 7 shows a preassembled unit of the first braking mechanism of the endoscope according to FIGS. 1 and 2.

In case of the first braking mechanism, as shown in FIGS. 3, 4 and 7, the corresponding (first) clip-in arms 18*a* are formed on an outer circumference of the corresponding (first) pressurizing element 16*a*. The (first) clip-in arms 18*a* of the first braking mechanism extend axially towards the first braking control element 7*a* and radially outwards. Their free ends are pushed axially against the rim of a pocket-shaped engagement structure formed by the first steering control element 6*a*. In case of the second braking mechanism, as shown in FIGS. 5 and 6, the corresponding (second) clip-in arms 18*b* are formed on an inner circumference of the corresponding (second) pressurizing element 16*b*. The (second) clip-in arms 18*b* of the second braking mechanism extend axially away from the second braking control element 7*b* and radially inwards in a hook-like manner. Their hook ends are pushed axially against the rim of an opening-shaped engagement structure formed by the second steering control element 6*b*.

In the stack of friction discs 17*a*, 17*b*, a number of steering side friction discs and a number of brake side friction discs are alternatingly stacked. The steering side friction discs form lugs extending radially outwards. In case of the first braking mechanism, this is best seen in FIG. 7. In case of the second braking mechanism, this is best seen in FIGS. 5 and 6. The lugs engage with a corresponding structure of the steering control element 6*a*, 6*b* to provide a non-rotatable and axially slidable connection between the steering-side friction discs and the steering control element 6*a*, 6*b*. The brake-side friction discs form lugs extending radially inwards to form a similar connection with a (selectively first or second) cam surface unit 19*a*, 19*b* of the friction fit assembly 14*a*, 14*b*. It is not excluded that instead of a stack of discs one disc can be used. The stack may comprise two discs. More discs increase the friction surfaces. However a properly structured disc (e.g. to prevent flexure) can apply or receive more pressure and thus be adequate for its function.

The (selectively first or second) cam surface unit 19*a*, 19*b* is arranged opposite to the pressurizing element 16*a*, 16*b*. The cam surface unit 19*a*, 19*b* has flat contact surfaces adapted to contact the stack of friction discs 17*a*, 17*b*. Thus, the stack of friction discs 17*a*, 17*b* is sandwiched between the pressurizing element 16*a*, 16*b* and the cam surface unit 19*a*, 19*b*. Further, the cam surface unit 19*a*, 19*b* extends axially inside the stack of friction discs 17*a*, 17*b* and engages with the brake side friction discs to form an axially slidable and non-rotatable connection.

The cam surface unit 19*a*, 19*b* is supported in an axially slidable and non-rotatable manner by a part fixed to the endoscope handle 2. In case of the first braking mechanism, the corresponding (first) cam surface unit 19*a* is supported on the central shaft 8, i.e. via a spline structure as shown in FIG. 3. In case of the second braking mechanism, the corresponding (second) cam surface unit 19*b* is supported on a pipe-like protrusion of the endoscope handle 2. Via the spring 15*a*, 15*b*, the cam surface is pushed towards a (selectively first or second) cam 20*a*, 20*b* formed by the braking control element 7*a*, 7*b*. When the braking control element 7*a*, 7*b* is rotated, the cam 20*a*, 20*b* is moved in a circumferential direction and slides along the cam surface, such that a circumferential movement of the cam 20*a*, 20*b* is transformed into an axial movement of the cam surface unit 19*a*, 19*b*.

That is, when the braking mechanism is in a non-activated state, as shown in FIGS. 3 and 5, the clip-in arms 18*a*, 18*b* of the pressurizing element 16*a*, 16*b* contact the rim of the steering control element 6*a*, 6*b*. The cam surface unit 19*a*, 19*b* can now move axially between the cam 20*a*, 20*b* and the stack of friction discs 17*a*, 17*b* by a clearance c and the friction discs are not pressed against each other.

Then, when the braking control element 7*a*, 7*b* including the cam 20*a*, 20*b* is rotated, the cam 20*a*, 20*b* pushes the cam surface unit 19*a*, 19*b* against the spring 15*a*, 15*b* towards the pressurizing element 16*a*, 16*b*. The spring 15*a*, 15*b* is compressed and a clearance c between the clip-in arms 18*a*, 18*b* of the pressurizing element 16*a*, 16*b* and the rim of the steering control element 6*a*, 6*b* occurs. Thus, as shown in FIGS. 4 and 6, the stack of friction discs 17*a*, 17*b* is compressed between the pressurizing element 16*a*, 16*b* and the cam surface unit 19*a*, 19*b* by a force of the spring 15*a*, 15*b*. A frictional fit between the brake-side friction discs and the steering-side friction discs is provided. The braking mechanism is activated.

When the braking control element 7*a*, 7*b* is rotated towards a non-activated position in order to loosen the braking mechanism, the cam 20*a*, 20*b* slides along the cam surface, releasing the cam surface unit 19*a*, 19*b*. As a result, the friction fit assembly 14*a*, 14*b* is pushed out of the steering control element 6*a*, 6*b* until the clip-in arms 18*a*, 18*b* of the pressurizing element 16*a*, 16*b* contact the rim of the steering control element 6*a*, 6*b*. Then, the force of the spring 15*a*, 15*b* does not act on the stack of friction discs 17*a*, 17*b* anymore, releasing the frictional fit between the brake-side friction discs and the steering-side friction discs.

Further, the first braking mechanism and the second braking mechanism provide different (selectively first or second) tactile structures 21*a*, 21*b*, which respectively define one or more intermediate braking positions.

Figure 8:
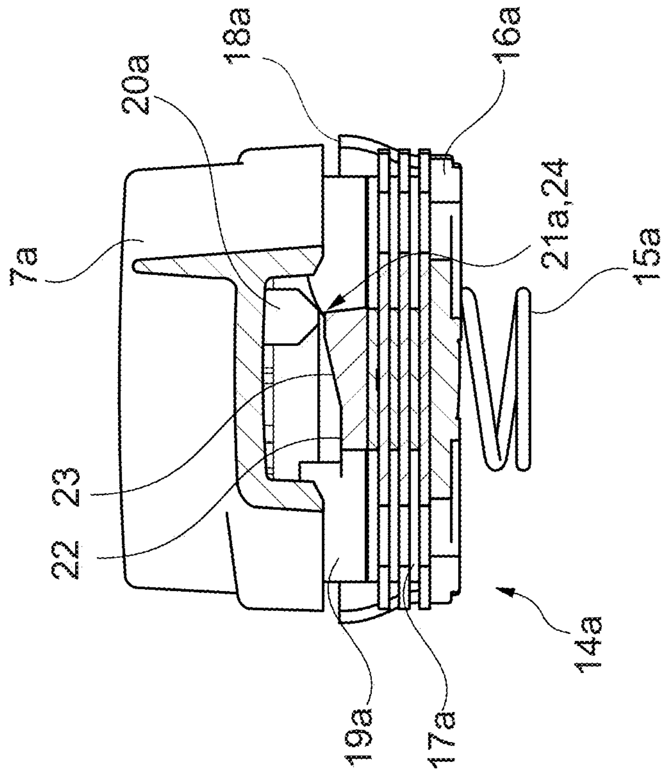
FIG. 8 shows the first braking mechanism according to FIG. 2 in a partial sectional side view.

In the first braking mechanism, the corresponding (first) tactile structure 21*a* is provided on the corresponding (first) cam surface. In this specific embodiment, as best seen in FIG. 7, the corresponding (first) cam surface unit 19*a* forms three first cam surfaces, adapted to contact the corresponding (first) cam 20*a*. Said first cam 20*a* is formed by the first braking control element 7*a*, as shown in FIG. 4. Each first cam surface essentially extends along a third of a circumference of the corresponding (first) cam surface unit 19*a*. Each first cam surface 20*a* subsequently has a first flat section 22, a first ramp section 23 extending circumferentially and axially towards the first braking control element 7*a*, an intermediate section 24 forming a recess in the first cam surface, a second ramp section 25 and a second flat section 26. The first flat section 22 and the second flat section 26 extend essentially orthogonally with respect to the control axis 9. The intermediate section 24 forms a first shoulder 24*a* adjacent to the first ramp section 23. Preferably, adjacent to the second ramp section 25, the intermediate section 24 further forms a second shoulder 24*b*, i.e. a surface having a steeper angle with respect to the circumferential direction than the second ramp section 25. In FIG. 8, which shows a partial sectional side view of the first braking mechanism, a state where the first braking control element 7*a* is positioned such that the first cam 20*a* contacts the intermediate section 24 of the first cam surface is illustrated.

Further, as seen in FIG. 7, the first cam surface unit 19*a* forms at least one, particularly three, circumferentially and axially extending stopper grooves 27 providing two circumferential stopper surfaces. Axially extending stopper pins 28 are formed integrally with the first braking control element 7*a* and, as shown in FIGS. 3 and 4, are received in said circumferentially extending grooves 27 to be slidable in the axial direction and in the circumferential direction. Thus, a relative rotation between the first braking control element 7*a* and the first cam surface unit 19*a* (and therefore the endoscope handle 2), is limited by a contact of the stopper pins 28 with the stopper surfaces of the stopper grooves 27. Further, the first braking control element 7*a* is formed integrally with the first cam 20*a* or cams (a number of cams corresponds to a number of cam surfaces), which extends axially towards the first cam surface unit 19*a*, having inclined or tapering contact edges. In particular, the first cam 20*a* is formed near a circumferentially inner surface of the first braking control element 7*a*.

Figure 9:
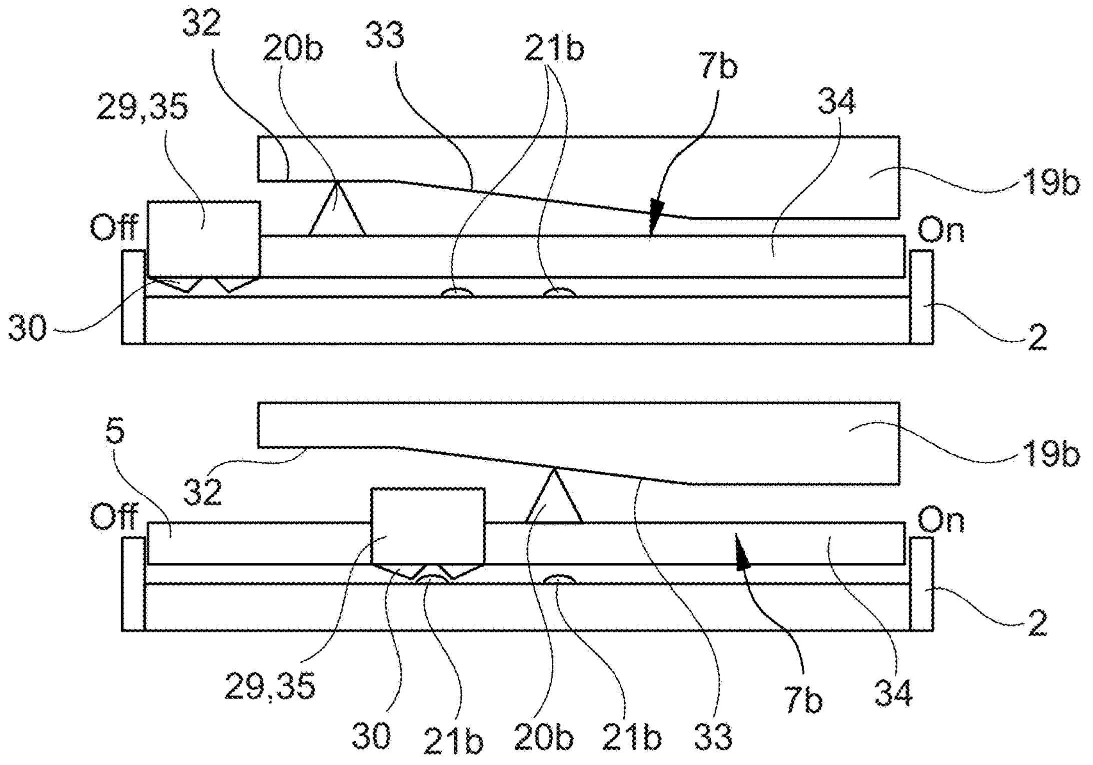
FIG. 9 shows a schematic illustration of a working principle of the second braking mechanism according to FIGS. 1 and 2.

A second tactile structure 21*b* provided by the second braking mechanism is described via the schematic side view shown in FIG. 9. In detail, FIG. 9 schematically shows an endoscope handle 2, provided with bumps or ribs serving as the second tactile structures 21*b*. The second braking control element 7*b* is supported on the endoscope handle 2 and has a lever portion 29. The lever portion 29 serves as a spring arm 35 and, facing towards the endoscope handle 2, forms a clicking structure 30 adapted to resiliently engage the second tactile structure 21*b*. On a side opposite to the clicking structure 30, the second braking control element 7*b* forms the second cam 20*b*. The second cam surface of the second cam surface unit 19*b* contacts the second cam 20*b* in the axial direction.

In the upper portion of FIG. 9, the second braking control element 7*b* is in an off-position and the lever portion 29 contacts a stopper flank 31 formed by the endoscope handle 2. In this position, the second cam 20*b* contacts a first flat surface 32 of the second cam surface, minimizing a distance between a friction element facing side of the second cam surface unit 19*b* and the second braking control element 7*b*. Thus, the second braking mechanism is inactive. In the lower portion of FIG. 9, the second braking control element 7*b* has been rotated to a first intermediate braking position. The clicking structure 30 formed on the lever portion 29 now engages a first bump or rib serving as one of the second tactile structures 21*b* of the second brake mechanism. The second cam 20*b* has slid approximately halfway along a ramp section 33 of the second cam surface unit 19*b*. Thus, the second cam surface unit 19*b* is pushed halfway towards the second friction element 17*b*, providing an intermediate braking force. The ramp section 33 of the second cam surface unit 19*b* has a continuous, linear ramp surface.

Figure 10:
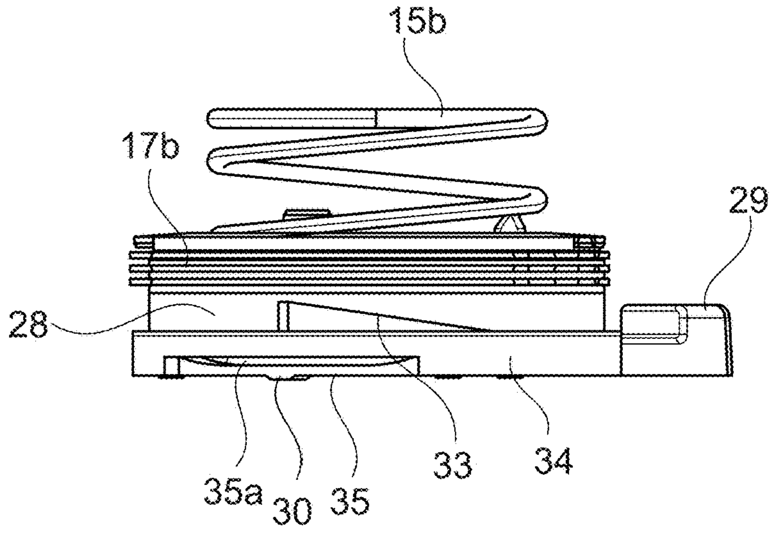
FIG. 10 shows the second braking mechanism according to FIGS. 1 and 2 in a side view.
Figure 11:
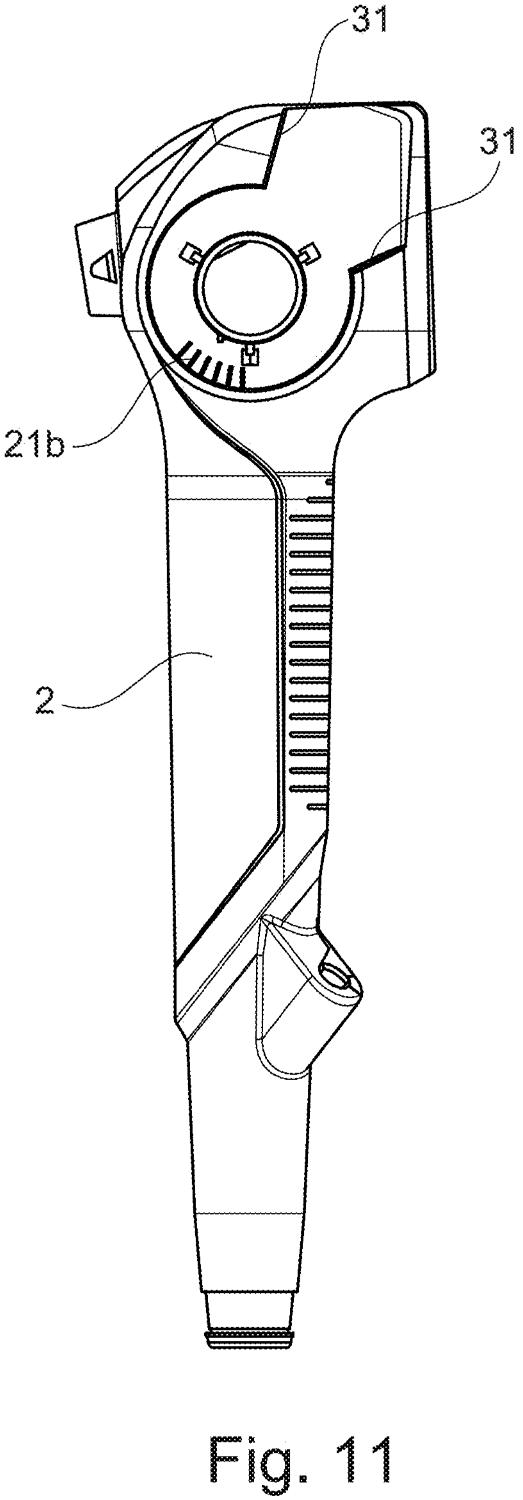
FIG. 11 shows an endoscope handle of the endoscope according to FIG. 1 in a disassembled state.
Figure 12:
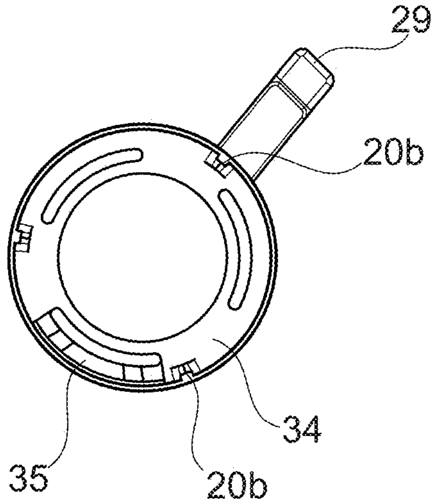
FIG. 12 shows a second breaking control element in a disassembled state.

The structure of the second braking mechanism can also be seen in FIG. 10. In particular, in this view, an alternative structure of the clicking structure 30 is shown. Slits 35*a* cut into a base portion 34 of the second braking control element 7*b* define flanks of a spring arm 35. On a lower side of the spring arm 35, the clicking structure 30 is formed as a bump extending towards the endoscope handle 2. When the bump or clicking structure 30 slides over an obstacle, the spring arm 35 will evade said obstacle and bend away from the obstacle. This is the case e.g. when the second braking mechanism is mounted to the endoscope handle 2 shown in FIG. 11, with the bumps or ribs (i.e. the second tactile structure 21*b*) serving as the obstacle. The bump-shaped clicking structure 30 formed at the second braking control element 7*b* slips between the bumps or ribs serving as the second tactile structure 21*b* and defining several intermediate braking positions. The second tactile structure 21*b* is formed on a supporting surface of the endoscope handle 2 housing which is recessed with respect to a surrounding housing part of the endoscope handle 2 in order to receive and support the second braking control element 7*b* as shown in FIG. 12 in a plan view. As shown in FIG. 11, diametrically opposite to the second tactile structure 21*b*, the supporting surface of the endoscope handle 2 opens at an angle in order to accommodate the lever portion 29 of the second braking control element 7*b*. Circumferential flanks next to the portion of the supporting surface of the endoscope handle 2 opening at an angle form the stopper flanks 31 adapted to contact the lever portion 29 laterally, thus limiting a rotation of the second braking control element 7*b* between the two stopper flanks 31. FIG. 11 further shows that the second braking control element 7*b* forms three second cams 20*b*.

As mentioned above, the braking mechanisms have tactile structures defining an intermediate braking position which is neither a full-braking position nor a non-braking position. Thus, in the intermediate braking position, the friction element is translated only partially along the control axis. The tactile structure may be any structure which provides a tactile feedback to the user that the intermediate braking position has been reached. The tactile structure can be a recess or a protrusion between the first and second ramp sections. The recess allows the cam to change the feedback provided as the control is rotated, as the cam dips into the recess. Alternatively, a protrusion between the first and second ramp sections would interrupt the rotation of the control momentarily, changing the force required for the cam to pass over the protrusion, thus providing tactile feedback. In the embodiment described with reference to FIG. 9 the clicking structure 30 resiliently engages the second tactile structure 21*b*, illustrated by a pair of bumps or ribs. Each of the bump or ribs generates a click therefore there are two intermediate brake positions. More or less bumps or ribs may be provided. The bumps or ribs can, alternatively, be positioned on the lever portion with the clicking structure formed in the handle. The intermediate section can be said to comprise the first and second ramp sections, where the bump or rib is aligned with a gap between them, even though the bump or rib is not placed on the intermediate section.

The following items are examples of various embodiments and variations thereof disclosed above, and others:

1. An endoscope (1) comprising: a proximal endoscope handle (2); an insertion cord extending from the endoscope handle (2) and configured to be inserted into a patient's body cavity, the insertion cord comprising an insertion tube (3), a bending section (4) and a distal tip unit (5); a steering mechanism configured to swivel the distal tip unit (5) by bending the bending section (4), and a braking mechanism configured to brake the steering mechanism, the steering mechanism comprising: a manually operable steering control element (6*a*), which is provided for receiving a steering input by a user and is rotatable around a control axis (9), and at least one steering wire (12*a*), which connects the bending section (4) with the steering control element (6*a*), and the braking mechanism comprising: a manually operable braking control element (7*a*) provided for receiving a braking input by the user, a friction element (17*a*) which is axially translatable in an axial direction defined by the control axis (9) to engage or disengage with the steering mechanism, and a cam pairing having a cam surface unit (19*a*) forming a cam surface and a cam (20*a*) contacting the cam surface in the axial direction, the cam (20*a*) being connected to or integrally formed with one of the braking control element (7*a*) and the friction element (17*a*) and the cam surface unit (19*a*) being connected to or integrally formed with the other one of the braking control element (7*a*) and the friction element (17*a*), the cam (20*a*) being configured to slide along the cam surface to transform the braking input into an axial translation of the friction element (17*a*), wherein the cam surface forms a first ramp section (23) for translating the friction element (17*a*) from a first braking position to an intermediate braking position, a second ramp section (25) for translating the friction element (17*a*) from the intermediate braking position to a second braking position, and an intermediate section (24) forming a tactile structure (21*a*), being arranged between the first ramp section

(23) and the second ramp section (25) and defining the intermediate braking position.

2. The endoscope (1) according to item 1, wherein the braking control element (7*a*) is rotatable around the control axis (9), the cam surface extends in a circumferential direction and the first ramp section (23) and the second ramp section (25) extend in the circumferential direction and in the axial direction.

3. The endoscope (1) according to item 2, wherein at least two, preferably three, cam surfaces are provided, which are dimensioned and arranged to form a circle around the control axis (9).

4. The endoscope (1) according to one of items 1 to 3, wherein the intermediate section (24) forms a projection and/or a recess at least with respect to the first ramp section (23).

5. The endoscope (1) according to one of items 1 to 4, wherein the intermediate section (24) forms a first shoulder or step adjacent to the first ramp section (23), a second shoulder or step adjacent to the second ramp section (25) and an intermediate flat surface arranged between the first shoulder or step and the second shoulder or step, with the first shoulder or step preferably having a steeper inclination than the second shoulder or step.

6. The endoscope (1) according to one of items 1 to 5, wherein the cam surface forms a first flat surface (22) at a position corresponding to the first braking position and/or a second flat surface (26) at a position corresponding to the second braking position.

7. The endoscope (1) according to one of items 1 to 6, wherein the first ramp section (23) and the second ramp section (25) have essentially the same inclination and a reference line extending from the first ramp section (23) is essentially tangential to the second ramp section (25) adjacent to the intermediate section (24).

8. The endoscope (1) according to one of items 1 to 7, wherein the cam (20*a*) is non-rotatably connected to the braking control element (7*a*) or formed integrally with the braking control element (7*a*), preferably on an inner axial or circumferential surface thereof.

9. The endoscope (1) according to item 8, wherein the cam (20*a*) has a contact edge which tapers in a direction towards the cam surface unit (19*a*).

10. The endoscope (1) according to one of items 1 to 9, wherein a pressurizing element (16*a*) is provided which supports a spring element (15*a*) on one axial side and the frictional element (17*a*) on another axial side, and the pressurizing element (16*a*) forms a stop surface (18*a*) acting in a direction opposite to the spring element (15*a*) and adapted to contact a rim portion of the steering control element (6*a*).

11. The endoscope (1) according to one of items 1 to 10, wherein the braking control element (7*a*) and the cam surface unit (19*a*) engage with each other via a circumferential stopping structure including a circumferentially extending stopper groove (27) providing two circumferential stopper surfaces and an axially extending stopper pin (28) which are slidable with respect to each other in the axial direction and in the circumferential direction.

12. The endoscope (1) according to one of items 1 to 11, further comprising a second steering mechanism configured to swivel the distal tip unit (5) by bending the bending section (4) in a second direction, comprising a second manually operable steering control element (6*b*), which is provided for receiving a second steering input by the user and is rotatable around the control axis (9), and at least one second steering wire (12*b*), which connects the bending section (4) with the second steering control element (6*b*), and a second braking mechanism configured to brake the second steering mechanism and comprising:

a manually operable second braking control element (7*b*) provided for receiving a second braking input by the user and being rotatable around the control axis (9), a second friction element (17*b*) which is axially translatable in the axial direction to engage or disengage with the second steering mechanism, and a second cam pairing having a second cam surface unit (19*b*), which forms a ramp section (33) of the second cam surface unit (19*b*), and a second cam (20*b*) contacting the ramp section (33) of the second cam surface unit (19*b*) in the axial direction, the second cam (20*b*) being connected to one of the second braking control element (7*b*) and the second friction element (17*b*) and the second cam surface unit (19*b*) being connected to the other one of the second braking control element (7*b*) and the second friction element (17*b*), the second cam (20*b*) being configured to slide along the ramp section (33) of the second cam surface unit (19*b*) to transform the second braking input into an axial translation of the second friction element (17*b*), wherein the second braking control element (7*b*) and a portion of the endoscope handle (2) form a click interface, said click interface including a click recess or click protrusion as a clicking structure (30), which is formed at one of the second braking control element (7*b*) and the portion of the endoscope handle (2), and a spring arm (35), which is formed at the other one of the second braking control element (7*b*) and the portion of the endoscope handle (2), is configured to engage with said clicking structure (30) and to resiliently bend away from said clicking structure (30).

13. The endoscope (1) according to item 12, wherein the second braking control element (7*b*) has a plate-like base portion (34), which forms the second cam surface or the second cam (20*b*) facing towards one side and which forms the spring arm (35) facing towards an opposing side.

14. The endoscope (1) according to item 13, wherein the spring arm (35) is formed from the base portion (34) of the second braking control element (7*b*) in the manner of a bridge formed between two longitudinal slits.

15. System comprising an endoscope (1) according to one of the items 1 to 14 and a monitor (M) connectable to the endoscope (1).

LIST OF REFERENCE NUMBERS

1 endoscope
2 endoscope handle
3 insertion tube
4 bending section
5 distal tip unit
6*a*, 6*b* first and second steering control elements
7*a*, 7*b* first and second braking control elements
8 central shaft
9 control axis
10 hollow shaft
11*a*, 11 b first and second wire drums
12*a*, 12*b* first and second steering wires
13 intermediate support portion
14*a*, 14*b* first and second friction fit assemblies
15*a*, 15*b* first and second springs
16*a*, 16*b* first and second pressurizing element

17*a*, 17*b* first and second stacks of friction discs/friction elements
18*a*, 18*b* first and second clip-in arms/stop surfaces
19*a*, 19*b* first and second cam surface units
20*a*, 20*b* first and second cams
21*a*, 21*b* first and second tactile structures
22 first flat section of the first cam surface
23 first ramp section of the first cam surface
24 intermediate section of the first cam surface
25 second ramp section of the first cam surface
26 second flat section of the first cam surface
27 stopper groove(s)
28 stopper pins
29 lever portion
30 clicking structure
31 stopper flank
32 first flat surface of the second cam surface
33 ramp section of the second cam surface unit
34 base portion
35 spring arm

We claim:

1. An endoscope comprising:

a handle;

an insertion cord extending from the handle and comprising an insertion tube, a bending section and a distal tip unit;

a steering mechanism comprising a steering control and a steering wire, the steering control being rotatable around a control axis, and the steering wire connecting the steering control with the bending section to bend the bending section when a user manually rotates the steering control; and a braking mechanism configured to brake the steering mechanism, the braking mechanism comprising:

a braking control operable to receive a braking input by the user;

a friction element which is axially translatable in an axial direction defined by the control axis to engage or disengage with the steering mechanism; and a cam pairing having a cam surface unit forming a cam surface and a cam contacting the cam surface in the axial direction, the cam being connected to or integrally formed with the braking control or the friction element, the cam surface unit being connected to or integrally formed with the other of the braking control or the friction element, wherein the cam surface comprises a first ramp section, a second ramp section, and an intermediate section laterally confined by a first shoulder adjacent to the first ramp section and a second shoulder adjacent to the second ramp section, the first shoulder defining a step-down transition from the first ramp section to the intermediate section and the second shoulder defining a step-up transition from the intermediate section to the second ramp section, the intermediate section extending between the first shoulder and the second shoulder and defining an intermediate braking position, wherein rotation of the braking control causes the cam to slide along the cam surface to transform the braking input into an axial translation of the friction element, and wherein the first ramp section translates the friction element from a first braking position to the intermediate braking position, and the second ramp section translates the friction element from the intermediate braking position to a second braking position.

2. The endoscope of claim 1, wherein the braking control is rotatable around the control axis, the cam surface extends in a circumferential direction and the first ramp section and the second ramp section extend in the circumferential direction and in the axial direction.

3. The endoscope of claim 2, wherein at least two cam surfaces are provided, which are dimensioned and arranged to form a circle around the control axis.

4. The endoscope of claim 1, wherein the first shoulder has a steeper inclination than the second shoulder.

5. The endoscope of claim 1, wherein the cam surface further comprises a first flat surface at a position corresponding to the first braking position and/or a second flat surface at a position corresponding to the second braking position.

6. The endoscope of claim 5, wherein the first ramp section comprises a first inclination angle, the second ramp section comprises a second inclination angle, and the first inclination angle and the second inclination angle differ by at most +/−5 degrees.

7. The endoscope of claim 6, wherein a reference line extending along and from the first ramp section is tangential to the second ramp section at a location where the second ramp section connects with the intermediate section.

8. The endoscope of claim 1, wherein the first ramp section comprises a first inclination angle, the second ramp section comprises a second inclination angle, and the second inclination angle is less than the first inclination angle.

9. The endoscope of claim 1, wherein the cam is non-rotatably connected to the braking control or formed integrally with the braking control.

10. The endoscope of claim 9, wherein the cam is non-rotatably connected to the braking control or formed integrally with the braking control on an inner axial or circumferential surface thereof.

11. The endoscope of claim 1, wherein the cam has a contact edge which tapers in a direction towards the cam surface unit.

12. The endoscope of claim 1, wherein a pressurizing element is provided which supports a spring element on one axial side and the friction element on another axial side, and wherein the pressurizing element forms a stop surface acting in a direction opposite to the spring element and adapted to contact a rim portion of the steering control.

13. The endoscope of claim 1, wherein the braking control and the cam surface unit engage with each other via a circumferential stopping structure including a circumferentially extending stopper groove providing two circumferential stopper surfaces and an axially extending stopper pin which are slidable with respect to each other in the axial direction and in the circumferential direction.

14. The endoscope of claim 1, further comprising:

a second steering mechanism comprising a second steering control rotatable around the control axis, and a second steering wire connecting the bending section with the second steering control to bend the bending section in the second direction when the user manually rotates the second steering control;

a second braking mechanism configured to brake the second steering mechanism and comprising:

a second braking control operable to receive a second braking input by the user and being rotatable around the control axis;

a second friction element which is axially translatable in the axial direction to engage or disengage with the second steering mechanism; and a second cam pairing having a second cam surface unit forming a ramp section and a second cam contacting the ramp section of the second cam surface unit in the axial direction to transform the second braking input into an axial translation of the second friction element, the second cam being connected to the second braking control or the second friction element, the second cam surface unit being connected to the other of the second braking control or the second friction element; and a click interface formed by the second braking control and a portion of the handle, the click interface including a click recess or click protrusion as a clicking structure, which is formed at the second braking control or the portion of the handle, and a spring arm, which is formed at the other of the second braking control or the portion of the handle, wherein the spring arm is configured to engage with the clicking structure to define an intermediate braking position of the second braking mechanism and to resiliently bend away from the clicking structure, and wherein the ramp section translates the second friction element from a first braking position to the intermediate braking position of the second braking mechanism and from the intermediate braking position to a second braking position.

15. The endoscope of claim 14, wherein the second braking control has a plate-like base portion, which forms the second cam surface or the second cam facing towards one side and which forms the spring arm facing towards an opposing side.

16. The endoscope of claim 15, wherein the spring arm is formed from the base portion of the second braking control in the manner of a bridge formed between two longitudinal slits.

17. A visualization system comprising an endoscope according to claim 1 and a monitor (M) connectable to the endoscope.

18. The endoscope of claim 1, further comprising a spring configured to preload the cam in an axial direction against the cam surface.

* * * * *